US012667241B2

(12) United States Patent
 Carpuat et al.

(10) Patent No.: US 12,667,241 B2
(45) Date of Patent: Jun. 30, 2026

(54) INSPECTION TOOL TO BE FITTED TO AN ENDOSCOPE

(71) Applicant: SAFRAN LANDING SYSTEMS, Velizy-Villacoublay (FR)

(72) Inventors: Bertrand Hunald Carpuat, Moissy-Cramayel (FR); Jessica Leslourdy, Moissy-Cramayel (FR)

(73) Assignee: SAFRAN LANDING SYSTEMS, Velizy-Villacoublay (FR)

( * ) Notice: Subject to any disclaimer, the term of this patent is extended or adjusted under 35 U.S.C. 154(b) by 242 days.

(21) Appl. No.: 18/566,357

(22) PCT Filed: May 25, 2022

(86) PCT No.: PCT/FR2022/050991
 § 371 (c)(1),
 (2) Date: Dec. 1, 2023

(87) PCT Pub. No.: WO2022/254128
 PCT Pub. Date: Dec. 8, 2022

(65) Prior Publication Data
 US 2024/0245282 A1 Jul. 25, 2024

(30) Foreign Application Priority Data
 Jun. 1, 2021 (FR) ..................................... 2105775

(51) Int. Cl.
 *A61B 1/00* (2006.01)
(52) U.S. Cl.
 CPC ...... *A61B 1/00101* (2013.01); *A61B 1/00087* (2013.01)

(58) Field of Classification Search
 CPC ............ A61B 1/00101; A61B 1/00087; A61B 1/0008
 See application file for complete search history.

(56) References Cited

U.S. PATENT DOCUMENTS

| | | | |
|---|---|---|---|
| 5,224,467 A * | 7/1993 | Oku ................... | A61B 1/00165 600/117 |
| 10,940,299 B2 | 3/2021 | Bareau et al. | |
| 2003/0181920 A1 | 9/2003 | Hawkins et al. | |
| 2015/0087911 A1 | 3/2015 | Konstorum et al. | |

OTHER PUBLICATIONS

International Search Report mailed Jul. 22, 2022, issued in corresponding International Application No. PCT/FR2022/050991, filed May 25, 2022, 5 pages.
Written Opinion mailed Jul. 22, 2022, issued in corresponding International Application No. PCT/FR2022/050991, filed May 25, 2022, 5 pages.

* cited by examiner

*Primary Examiner* — Hwa Andrew Lee
(74) *Attorney, Agent, or Firm* — CHRISTENSEN O'CONNOR JOHNSON KINDNESS PLLC

(57) ABSTRACT

An inspection tool configured to be fitted to an endoscope includes a body with an attachment portion configured to be attached to one end of the endoscope, and an opening. The tool further includes a transparent element with at least one visual reference mark having a calibrated dimension, wherein the transparent element is mounted at the opening in the body.

8 Claims, 5 Drawing Sheets

INSPECTION TOOL TO BE FITTED TO AN ENDOSCOPE

FIELD OF THE DISCLOSURE

The disclosure relates to an inspection tool intended to be fitted to an endoscope, an assembly comprising such a tool, and a method for inspecting a hollow part with the use of such an assembly.

BACKGROUND

Such a tool and such a method can be used in particular in the context of manufacturing hollow parts comprising an internal surface which must be covered with a coating, for example chrome plating. Quality control of the coating deposited on the internal surface is generally carried out using an endoscope.

Such an endoscope conventionally includes an end equipped with an observation head comprising lighting means and image capturing means. The images obtained using such an endoscope allow viewing whether an indication is present in the coating. Such an indication is a scratch or a cavity, for example.

It is currently difficult to characterize such indications, in particular to know their dimensions. Consequently, as soon as such indications are present, then either the coating is changed by removing the coating and depositing a new coating, or the part is scrapped, which reduces the manufacturing rate of such parts and increases manufacturing costs.

Furthermore, it is also necessary to be able to inspect parts whose surface to be inspected is uncoated. In such a case, it may be useful to decide on whether or not it is necessary to retouch the surface or to scrap the part.

SUMMARY

In order to remedy these disadvantages, the disclosure proposes an inspection tool intended to be fitted to an endoscope, characterized in that it includes a body comprising an attachment portion intended to be attached to one end of the endoscope and an opening, and a transparent element comprising at least one visual reference mark of calibrated size, the transparent element being mounted at the opening in the body.

Such an inspection tool can be mounted on one end of an endoscope comprising an observation head, so that the opening of the body and the transparent element are located facing the observation head.

The inspection tool and the corresponding end of the endoscope can then be inserted into a hollow part, so that the observation head is positioned facing an indication to be measured on an internal surface of the hollow part, and so that the visual reference mark is located at or near the indication. Such an indication is for example a scratch or cavity present in the internal surface to be inspected of the hollow part.

The dimension(s) of the indication can then be determined by comparison with known dimensions of the visual reference mark(s).

The visual reference mark may be a geometric shape that is solid or an outline, for example a circle, a disk, or a polygon.

The visual reference mark may be a graduated scale. The visual reference mark may be an indication of an angle, for example a degree wheel. The visual reference mark may be a curve with a calibrated profile, for example a curve of a sinusoidal or polynomial function, etc. The body may be hollow, at least in part. The body may have an open end enabling insertion of the corresponding end of the endoscope.

The inspection tool may comprise a locking member removably attached to the body at the opening, the transparent element being attached to the body by wedging it between the locking member and the body.

Alternatively, the transparent element may be attached by other means of attachment, for example by screwing, gluing, or welding.

Such attachment of the transparent element is easy and fast to implement.

The locking member may be attached by snap-fitting to the body.

The locking member may include an opening located in line with the opening of the body, the transparent element extending in front of the opening of the locking member.

The locking member may have a general U-shape comprising a middle portion having the opening and two arms extending one on either side of the middle portion.

The arms may be attached by snap-fitting to the body.

The transparent element may have two ends, and each end can be wedged between a side arm of the locking member and the body.

Each side arm may comprise an area forming a hook, meaning with a projecting portion, engaging with a recessed area of the body, or vice versa, so as to implement the snap-fitting. The middle portion or the side arms may be deformable to facilitate assembly by snap-fitting. Additionally or alternatively, the corresponding portion of the body used for the assembly by snap-fitting may be deformable.

The body may extend along a longitudinal axis, the opening of the body being located on a side surface of the body.

The longitudinal axis may correspond to the axis of insertion of the tool.

The body may be cylindrical, at least in part, with the opening located at a cylindrical side surface of the body.

The transparent element may be a flexible sheet.

The use of a flexible sheet makes it possible to adapt its curvature so that, once the tool has been inserted into the part to be inspected, this sheet can be applied against the surface to be inspected, at a contact area containing the visual reference mark. During such an application, the sheet can deform freely from the contact pressure, so as to fit against the surface to be inspected.

The transparent element may comprise a contact area extending beyond the body.

In the case of a cylindrical body for example, the contact area of the transparent element may extend beyond the cylindrical surface of the portion comprising the opening, in the radial direction. The radial direction is defined as the direction perpendicular to the axis of the cylindrical body, also called the longitudinal axis.

This ensures that contact is possible between the transparent element and the surface to be inspected.

Alternatively, the transparent element may not have a contact area and may be set back from the external surface of the body. In other words, contact against the internal surface then occurs on the body only and not on the transparent element.

In this case, it is necessary to know and be in control of the distance between the surface to be inspected and the visual reference mark present on the transparent element, in order to be able to deduce the size of the indication on the surface to be inspected.

For example, the transparent element may be inserted into a slot surrounding the opening of the body, so as to keep the transparent element at a distance from the external surface of the body, for example at a distance from a radially cylindrical external surface of the body.

The transparent element may comprise at least two reference marks of different dimensions. Alternatively, the transparent element may comprise a single reference mark.

The two reference marks are for example two circles or disks, or two polygons of different sizes, for example a first circle or disk of about 0.2 mm in size and a second circle or disk of about 0.5 mm in size.

In this manner, it is possible for example to compare an indication to each of these reference marks, so as to determine whether the indication has a smaller dimension than a first reference mark, a larger dimension than a second reference mark, or a dimension between those of the first and second reference marks.

The transparent element may comprise several reference marks that are offset from each other. Such a feature allows compensating for a possible erasure of one or more reference marks due to friction during use of the tool. Thus, in the event of total or even partial deletion of one of the reference marks, it is possible to use another one.

In this case, at least two reference marks offset from each other may be identical or of the same size.

The attachment portion may comprise removable attachment means configured to enable attachment to the endoscope.

The removable attachment means may comprise a thrust screw or clamping attachment means, for example.

The clamping attachment means may comprise at least one elastically deformable tab, configured to come to bear against a surface of the endoscope, and a nut configured to act on the tab so as to deform it. The nut may cooperate with a thread of the body. Tightening the nut thus generates deformation of the tab so that the tab generates friction, ensuring attachment of the body on the endoscope. Conversely, loosening the nut releases the tab which returns to its original position so that the inspection tool can be released from the endoscope.

The opening of the body may be formed by a window of generally rectangular shape.

The opening of the locking member may be formed by a window of generally rectangular shape.

The disclosure also relates to an assembly comprising an endoscope comprising an end including an observation head, characterized in that the assembly comprises a tool of the aforementioned type, mounted on the end so that the observation head is located facing the opening of the body.

The endoscope may comprise lighting means and image capture means, as is known per se. The image capture means may include a lens. The lens may have a fixed focal length. Even in the case of a lens with an adjustable focal length, the disclosure makes it possible to fix such a focal length. By extension, the lens is then said to have a fixed focal length.

The disclosure relates to a method for inspecting a hollow part with the help of an assembly of the aforementioned type, comprising the following steps:

inserting the observation head and the inspection tool into the hollow part, positioning the observation head facing an indication to be measured on an internal surface of the hollow part, so that the visual reference mark is located at or near the indication, determining at least one characterization of the indication with the help of the visual reference mark.

The characterization may be a dimension.

The observation head may be positioned so that the transparent element is in contact with the internal surface.

The internal surface of the hollow part may be covered, at least in part, with a coating.

Alternatively, the part may not be covered by a covering.

Such a coating may be obtained by chrome plating of the internal surface. Alternatively, such a coating may be obtained by a process such as chromic acid anodizing, sulfuric acid anodizing, cadmium plating, nickel plating, high velocity oxygen-fuel coating (HVOF), etc. If the indication, for example a scratch or a cavity, has dimensions that are too large, then the coating can be removed, in whole or in part, and a new coating can then be deposited on the internal surface. Alternatively, the part can be scrapped in the event of non-compliance, meaning the dimensions of the indication are too large.

Alternatively, the surface can be locally repaired.

Conversely, if the dimensions of the indication are less than some determined specifications, then the part and the covering can be kept as is.

Removal of the coating can be carried out by stripping, for example by chemical stripping.

DETAILED DESCRIPTION

Figure 1:
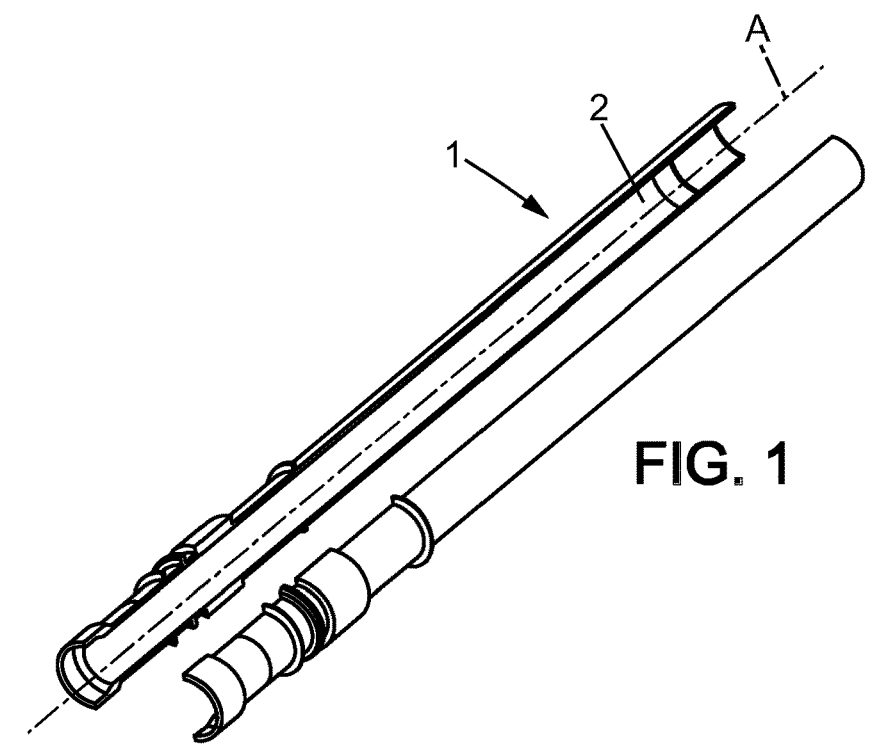
FIG. 1 is a perspective section view of a hollow part to be inspected.

FIG. 1 illustrates a hollow part 1 extending along an axis A and of generally cylindrical shape. Part 1 comprises a cylindrical internal surface 2 covered in whole or in part by a coating resulting from a chrome plating process. Part 1 is for example a cylinder intended to equip a landing gear. Of course, the disclosure is not limited to this type of part. In order to be able to visually inspect for and characterize possible defects or indications in the coating of internal surface 2, for example such as scratches or cavities in the coating, the disclosure proposes fitting an endoscope with an inspection tool 3 for which a first embodiment is illustrated in FIGS. 1 to 6.

Figure 2:
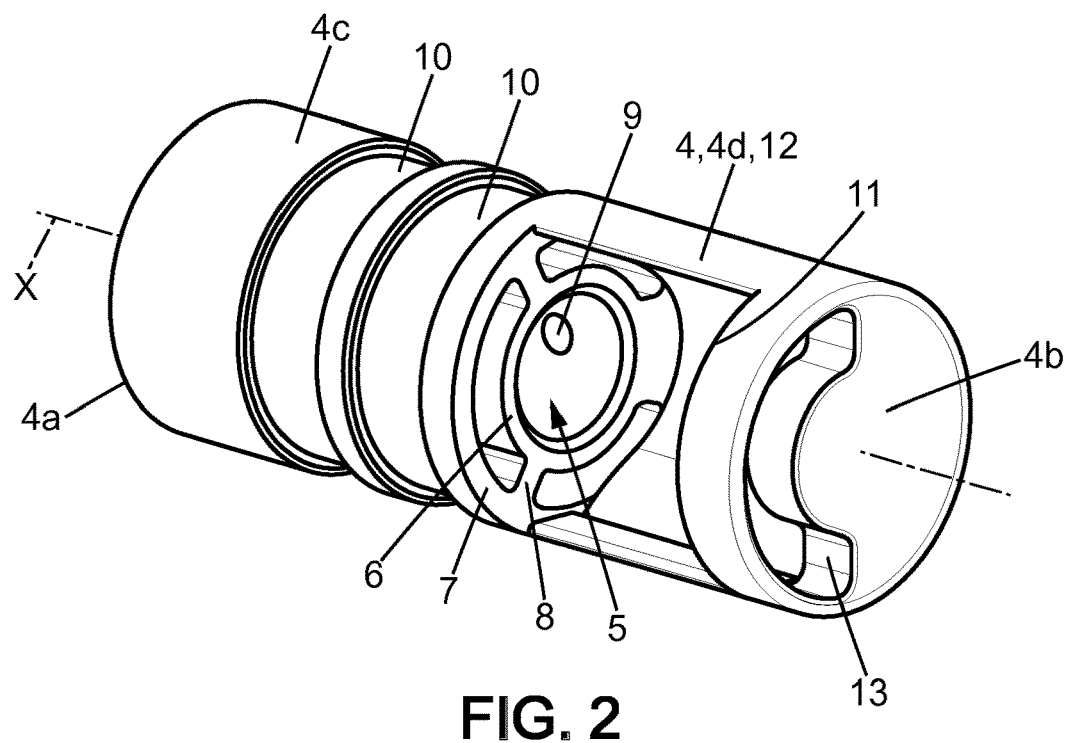
FIG. 2 is a perspective view of a body of an inspection tool according to a first embodiment.
Figure 3:
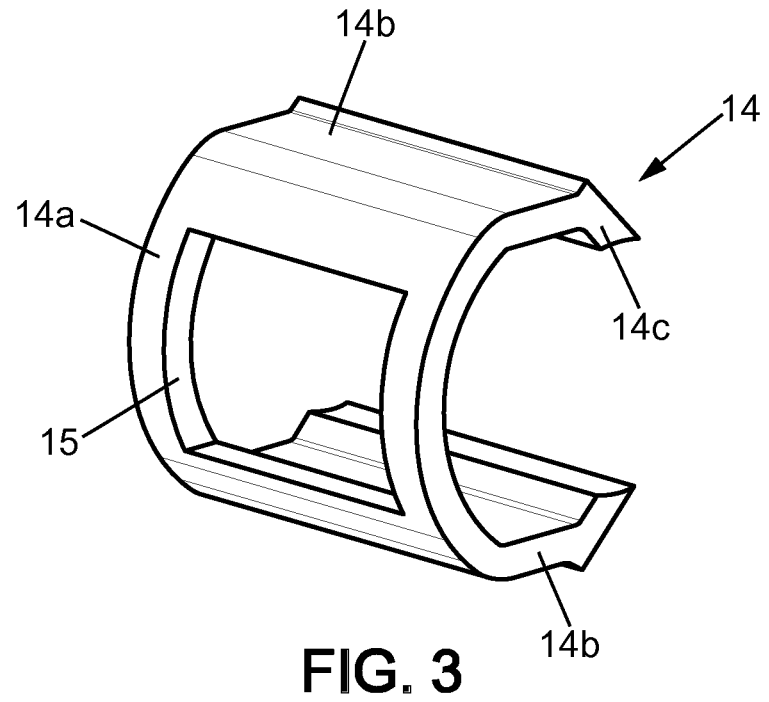
FIG. 3 is a perspective view of a locking member of the inspection tool.
Figure 4:
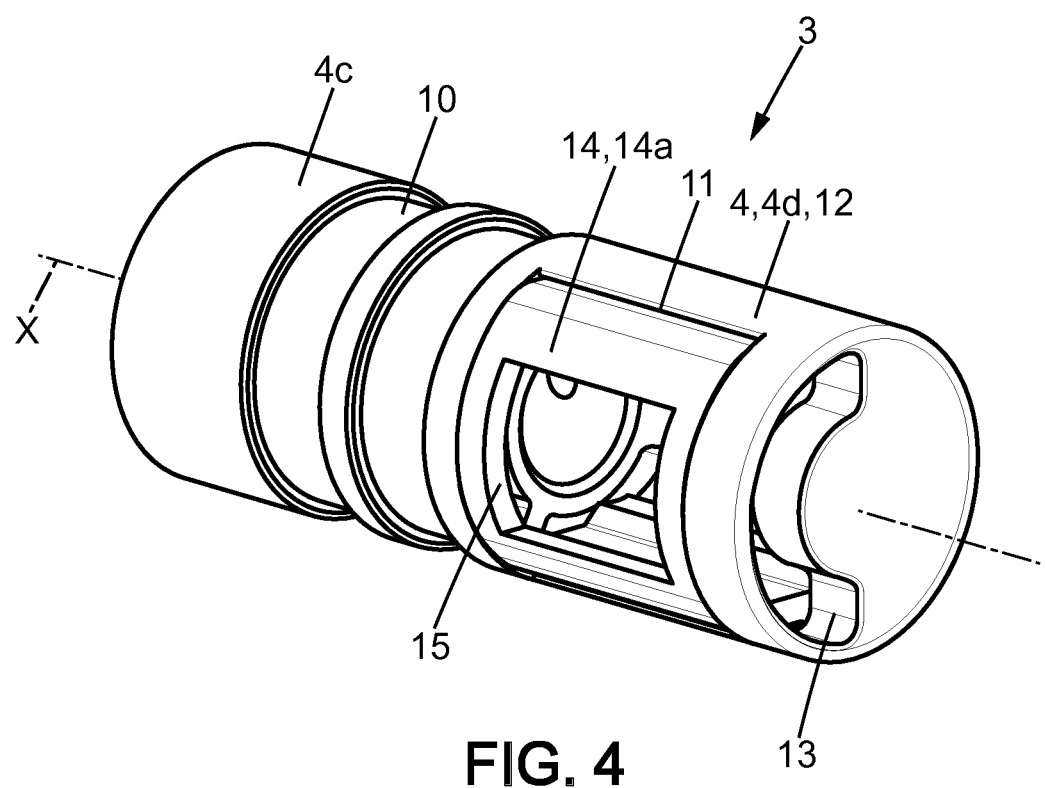
FIG. 4 is a perspective view of the inspection tool.
Figure 5:
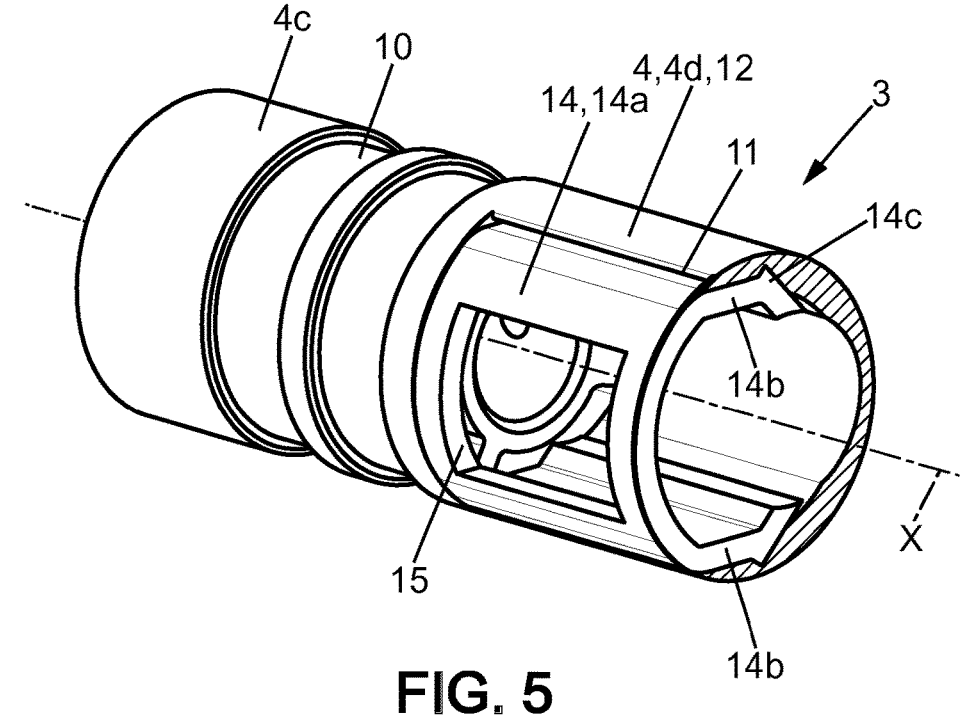
FIG. 5 is a perspective section view of the inspection tool, the section plane being radial and passing in particular through the arms of the locking member.

Inspection tool 3 comprises a body 4, which can be seen in particular in FIG. 2.

Body 4 has a generally cylindrical shape and extends along a longitudinal axis X. The terms axial, radial, and circumferential are defined in relation to this longitudinal axis X.

Body 4 is hollow and has a first end 4*a* and a second end 4*b*. The portion of body 4 located towards first end 4*a* is referred to as the proximal portion 5 of body 4 and the portion of body 4 located towards second end 4*b* is referred to as the distal portion 4*d* of body 4.

Proximal portion 4*c* comprises a cylindrical hole 5 intended for insertion of the end of the endoscope, this end of the endoscope being fitted with an observation head as is known per se. The observation head is oriented radially, meaning in the direction perpendicular to the general direction of extension of the endoscope. Hole 5 is defined by a radially internal cylindrical wall 6, connected to a radially external cylindrical wall 7 by means of radial dividers 8.

In this type of embodiment, tool 3 is attached to the corresponding end of the endoscope by means of a thrust screw, not shown, engaged in a tapping 9 of body 4 which traverses a radial divider 8. Alternatively, walls 6 and dividers 8 can be combined.

Proximal portion 4*c* of body 4 further comprises two external annular grooves 10, offset axially from one another, so as to limit the contact surface area between tool 3 and the surface to be inspected, and so as to lighten the tool 3.

Distal portion 4*d* of body 4 further comprises an opening or window 11 in its radially external wall 12. Opening 11 has a generally rectangular shape and is intended to be located axially and circumferentially facing the observation head of the endoscope.

Second end 4*b* of body 4 further comprises a slot 13 in the form of an arc which is open to the internal volume of distal portion 4*d* of body 4 and allows any external light to travel through to tool 3 and facilitate the dismantling of locking member 14 and sheet 16. The inside diameter of hole 5 of proximal portion 4*c* is less than the inside diameter of external wall 12 of distal portion 4*d*.

Tool 3 further comprises a locking member 14 intended to be removably mounted by snap-fitting, at opening 11 of distal portion 4*d* of body 4. Locking member 14 has a generally U-shaped cross-section, comprising a middle portion 14*a* in the form of a cylindrical portion and two arms 14*b*, extending one on either side of middle portion 14*a*. Each arm 14 is rectilinear and has a hook 14*c* at its free end. Each hook 14*c* is formed by a projecting portion which engages by snap-fitting into a recessed portion formed in body 4. Middle portion 14*a* comprises an opening or window 15, of generally rectangular shape, located axially and circumferentially facing opening or window 11 of distal portion 4*d* of body 4.

Arms 14*b* and/or middle portion 14*a* of locking member 14 are elastically deformable so as to allow snap-fitting onto body 4.

A transparent sheet 16 (visible only in FIG. 6) covers locking member 14, in particular opening 15 of locking member 14. Sheet 16 has two ends 16*a*, 16*b*, wedged and fixedly held between arms 14*b* of locking member 14 and body 4, when locking member 14 is snap-fitted onto body 4. One will note that sheet 16 can extend beyond arms 14*b* so that its free ends protrude into the internal volume of distal portion 4*d* of body 4.

Once mounted on body 4 by means of locking member 14, sheet 16 is curved and extends at least partly radially outside distal portion 4*d* and middle portion 14*a*.

Figure 6:
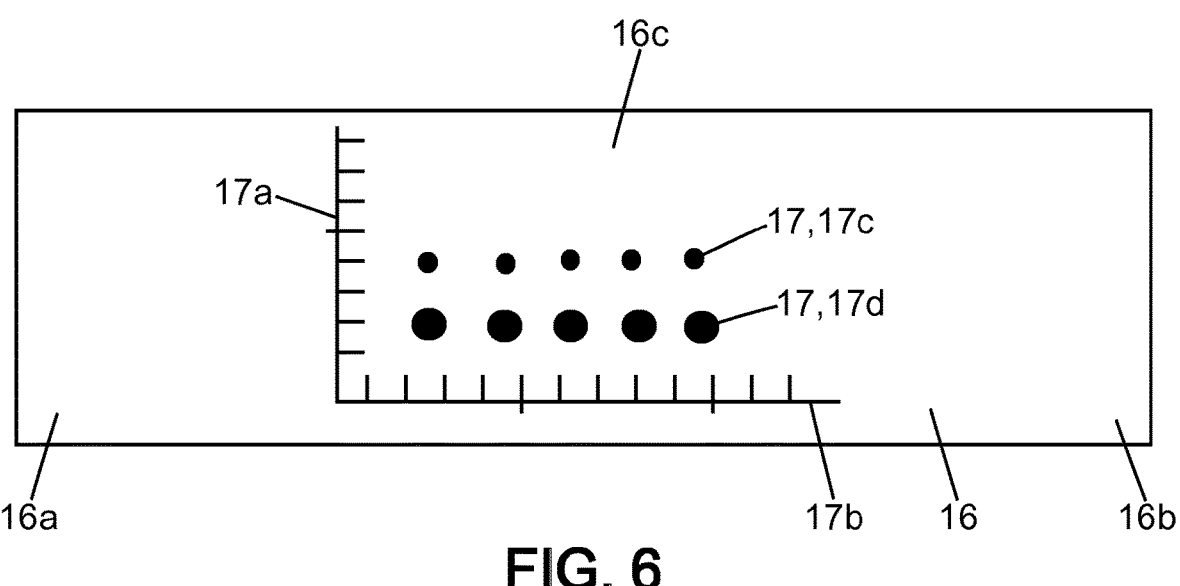
FIG. 6 is a front view of a transparent sheet comprising visual reference marks.
Figure 7:
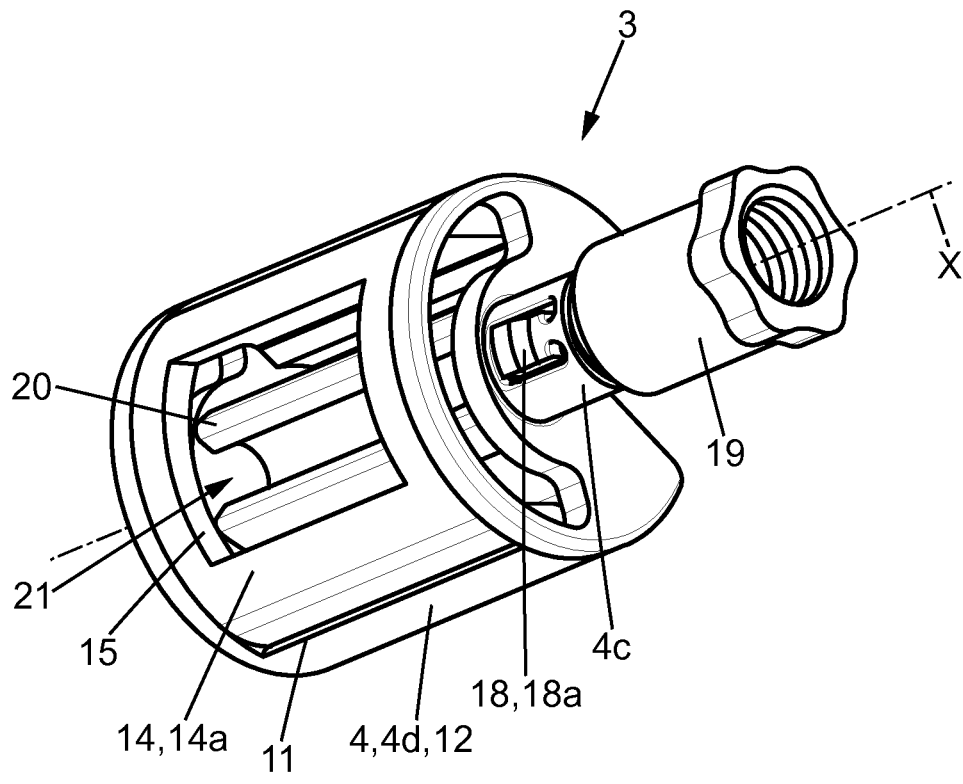
FIG. 7 is a perspective view of an inspection tool according to a second embodiment.
Figure 8:
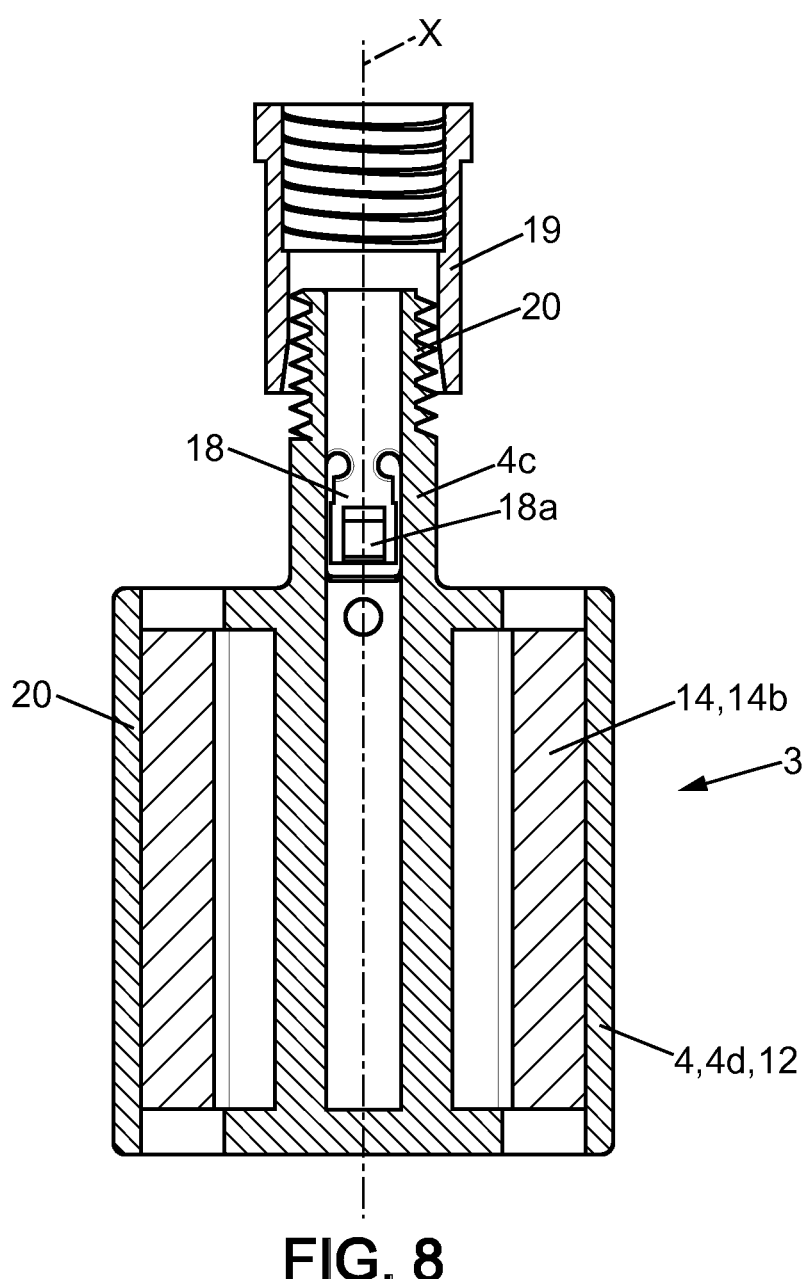
FIG. 8 is a longitudinal section view of the inspection tool of FIG. 7.

Sheet 16 further comprises a middle portion 16*c* comprising at least one visual reference mark 17, as illustrated in FIG. 6. In the embodiment illustrated in FIG. 6, sheet 16 has a generally rectangular shape and the middle portion of sheet 16 comprises several visual reference marks 17, in particular a graduated ruler 17*a* extending in a first direction, a graduated ruler 17*b* extending in a second direction perpendicular to the first direction, and several pairs of discs 17*c*, 17*d*, offset circumferentially relative to one another. Each pair of disks comprises a first disk 17*c* and a second disk 17*d* which are offset axially relative to one another. The diameter of first disk 17*c* is less than the diameter of second disk 17*d*. FIGS. 7 and 8 illustrate an inspection tool 3 according to another embodiment, which differs from the one described previously with reference to FIGS. 2 to 6 in that the proximal portion 4*c* of body 4 is a tubular portion of smaller diameter than distal portion 4*d*, the proximal portion 4*c* comprising deformable tabs 18 extending axially and configured to be deformed between an attachment position and a release position.

In the attachment position, free end 18*a* of each tab 18 extends radially inside proximal portion 4*c* so as to engage with the corresponding end of the endoscope. Conversely, in the release position, tabs 18 do not engage with the endoscope.

A nut 19 is mounted on an external thread 20 of proximal portion 4*c* of body 4, nut 19 being able to force tabs 18 towards their attachment position. Tightening and loosening nut 19 therefore makes it possible to move nut 19 axially while deforming or actuating tabs 18.

Furthermore, in this embodiment, distal portion 4*d* comprises a cylindrical internal part 20, which can be of the same diameter as proximal portion 4*c* and which lies within its extension, the internal portion 20 having a slot 21 extending axially and located circumferentially facing window 11 of distal portion 4*d* and window 15 of locking member 14.

Thus, when using such an inspection tool 3, sheet 16 is mounted on body 4 by means of locking member 14 so that it extends radially outside external cylindrical surface 12 of distal portion 4*d* and middle portion 14*a*.

Furthermore, the end of the endoscope is inserted into body 4 so that the observation head is located and oriented facing windows 11, 15 of body 4 and locking member 14, then body 4 is attached to the endoscope by means of the thrust screw or by actuation of nut 19.

Tool 3 and the end of the endoscope are then inserted axially into part 1 to be inspected and are oriented circumferentially so as to place windows 11, 15 and the observation head facing a possible indication to be characterized.

A more fine-tuned adjustment then allows placing one of visual reference marks 17 in line with or near the indication to be characterized so as to be able to determine its dimension. Once in position, flexible sheet 16 is in contact with surface 2 to be inspected.

In the case of sheet 16 illustrated in FIG. 6, it is possible for example to consider that if the dimension of the indication is less than the diameter of second disk 17*d* or the diameter of first disk 17*c*, then part 1 is considered to be compliant.

Conversely, if the indication has dimensions that are too large, then part 1 can be considered non-compliant.

The invention claimed is:

1. An assembly, comprising;
    an endoscope comprising one end including an observation head;
    an inspection tool fitted to said endoscope, said tool including a body comprising an attachment portion attached to said end of the endoscope and an opening; and a transparent element comprising at least one visual reference mark of calibrated size, said transparent element being mounted at the opening in the body, the observation head of the endoscope being located facing the opening of the body of the tool, wherein the tool further comprises a locking member removably attached to the body at said opening, and said transparent element is attached to the body by wedging the transparent element between said locking member and the body, or wherein the transparent element is attached to the body by screwing, gluing, or welding.

2. The assembly according to claim 1, wherein the body extends along a longitudinal axis (X), the opening of the body being located on a side surface of the body.

3. The assembly according to claim 1, wherein the transparent element comprises a contact area extending beyond the body.

4. The assembly according to claim 1, wherein said transparent element comprises at least two reference marks of different dimensions.

5. A method for inspecting a hollow part with the help of the assembly according to claim 1, the method comprising the following steps:

inserting the observation head and the inspection tool into the hollow part, positioning the observation head facing an indication to be measured on an internal surface of said hollow part so that the visual reference mark is located at or near said indication, and determining at least one characterization of the indication with the help of the visual reference mark.

6. The method according to claim 5, wherein the internal surface of said hollow part is covered, at least in part, with a coating.

7. An assembly, comprising;

an endoscope comprising one end including an observation head;

an inspection tool fitted to said endoscope, said tool including a body comprising an attachment portion attached to said end of the endoscope and an opening; and a transparent element comprising at least one visual reference mark of calibrated size, said transparent element being mounted at the opening in the body, the observation head of the endoscope being located facing the opening of the body of the tool, wherein the transparent element is a flexible sheet.

8. A method for inspecting a hollow part with the help of an assembly, the method comprising the following steps:

inserting the observation head and the inspection tool into the hollow part, positioning the observation head facing an indication to be measured on an internal surface of said hollow part so that the visual reference mark is located at or near said indication, and determining at least one characterization of the indication with the help of the visual reference mark, wherein the assembly, comprises;

an endoscope comprising one end including an observation head;

an inspection tool fitted to said endoscope, said tool including a body comprising an attachment portion attached to said end of the endoscope and an opening; and a transparent element comprising at least one visual reference mark of calibrated size, said transparent element being mounted at the opening in the body, the observation head of the endoscope being located facing the opening of the body of the tool, wherein the observation head is positioned so that the transparent element is in contact with the internal surface.

* * * * *